US011278295B1

(12) United States Patent
McCorkell

(10) Patent No.: US 11,278,295 B1
(45) Date of Patent: Mar. 22, 2022

(54) CUFF DEVICE FOR ACCESSING PATIENT BLOOD VESSELS

(71) Applicant: Crystal McCorkell, Raleigh, NC (US)

(72) Inventor: Crystal McCorkell, Raleigh, NC (US)

( * ) Notice: Subject to any disclaimer, the term of this patent is extended or adjusted under 35 U.S.C. 154(b) by 0 days.

(21) Appl. No.: 17/308,150

(22) Filed: May 5, 2021

Related U.S. Application Data

(60) Provisional application No. 63/109,479, filed on Nov. 4, 2020.

(51) Int. Cl.
*A61B 17/132* (2006.01)
*A61M 5/42* (2006.01)
*A61B 5/15* (2006.01)

(52) U.S. Cl.
CPC .... *A61B 17/1325* (2013.01); *A61B 5/150068* (2013.01); *A61M 5/425* (2013.01)

(58) Field of Classification Search
CPC .......... A61B 17/1325; A61B 5/150068; A61B 17/135; A61B 17/1355; A61M 5/427; A61M 1/3655; A61M 29/00; A61M 5/425; A61H 15/0078; A61H 2015/0014; A61H 2201/165
See application file for complete search history.

(56) References Cited

U.S. PATENT DOCUMENTS

| 9,730,704 | B2* | 8/2017 | Rose | A61B 17/1322 |
| 2007/0135836 | A1* | 6/2007 | McEwen | A61B 17/135 |
| | | | | 606/203 |
| 2009/0234261 | A1* | 9/2009 | Singh | A61B 17/1325 |
| | | | | 601/152 |

* cited by examiner

*Primary Examiner* — Brandy S Lee
(74) *Attorney, Agent, or Firm* — Ashley D. Johnson; Dogwood Patent and Trademark Law

(57) ABSTRACT

The presently disclosed subject matter is generally directed to a device that can be used as a tourniquet cuff for effective blood draws and IV insertion. The disclosed device assists skilled medical professionals in locating a vessel and inserting an intravenous tube, catheter, and/or blood drawing needle therein. Particularly, the device includes a cuff that wraps around at least a portion of a patient limb (e.g., an arm). The cuff is secured on the patient's limb with a plurality of straps that are tightened and secured about the circumference of the cuff. When the device is configured on the limb of a patient, the patient's blood vessels immediately engorge with blood. In this way, the vessels can be clearly visualized by or felt by a medical professional. As a result, blood can easily and efficiently be drawn and/or an IV successfully inserted without multiple attempts at finding the vessel.

20 Claims, 11 Drawing Sheets

CUFF DEVICE FOR ACCESSING PATIENT BLOOD VESSELS

CROSS-REFERENCE TO RELATED APPLICATIONS

This application claims priority to U.S. Provisional Patent Application No. 63/109,479 filed Nov. 4, 2020, the entire content of which is incorporated by reference herein.

TECHNICAL FIELD

The presently disclosed subject matter relates generally to a cuff device for accessing patient blood vessels, and to methods of making and using the disclosed device.

BACKGROUND

One of the most frequently performed medical procedures is the insertion of a needle into a live human body for the purpose of drawing blood from a vessel, delivering fluids and drugs, inserting a catheter, performing diagnostic tests, and the like. Conventionally, clinicians use anatomical landmarks to estimate the location of blood vessels based on a position of visible features (such as articulations and muscles) and palpation of non-visible structures. Despite the frequency of this procedure, accurate needle insertion is often challenging due to the difficulty in locating a desired blood vessel in some patients. For example, due to excess skin and fatty tissue, blood vessels are frequently difficult to visualize in obese and overweight patients. In addition, because their blood vessels are small, the location of vessels in children has also proven challenging. Further, low blood pressure can make it difficult to locate vessels in elderly and ailing patients. As a result, several attempts are frequently made to find an acceptable vessel, which is inefficient, time-consuming, and leads to potential injury and patient discomfort. It would therefore be beneficial to provide an improved device and technique to assist a practitioner when locating a vein that would otherwise be difficult to detect in a patient.

SUMMARY

In some embodiments, the presently disclosed subject matter is directed to a device for use in accessing blood vessels in a patient. Particularly, the device comprises a cuff defined by a plurality of side edges, a top face, and a bottom face. The device includes a first strap defined by a first end and a second end with a length therebetween, wherein the first end of the first strap is attached to a first side edge of the cuff. The device includes a second strap defined by a first end and a second end with a length therebetween, wherein the first end of the second strap is attached to a second side edge of the cuff. The first cuff side edge is directly opposed to the second side edge of the cuff.

In some embodiments, the first end of the first strap and the first end of the second strap are separated by about 180 degrees.

In some embodiments, the cuff has a length of about 5-10 inches, a width of about 2-6 inches, and a thickness of about 0.03-1 inch.

In some embodiments, the first and second straps each have a length of about 20-60 inches, a width of about 0.5-2 inches, and a thickness of about 0.03-1 inch.

In some embodiments, at least one of the first strap, second strap, and cuff are constructed from an elastic material.

In some embodiments, the device is latex-free.

In some embodiments, the bottom face of the cuff comprises a padding material selected from foam, polymeric material, mesh, rubber, silicone, or combinations thereof.

In some embodiments, the presently disclosed subject matter is directed to a kit comprising a plurality of cuffs, each cuff defined by a plurality of side edges, a top face, and a bottom face. The kit further includes a plurality of straps, each strap comprising a first end and a second end with a length therebetween. The first end of each strap is releasably attachable to a side edge of a corresponding cuff. The plurality of cuffs and straps are configured in a variety of shapes, sizes, materials, or combinations thereof.

In some embodiments, each cuff has a length of about 5-10 inches, a width of about 2-6 inches, and a thickness of about 0.03-1 inch.

In some embodiments, each strap has a length of about 20-60 inches, a width of about 0.5-2 inches, and a thickness of about 0.03-1 inch.

In some embodiments, at least one strap and cuff are constructed from an elastic material.

In some embodiments, at least one strap and cuff are latex-free.

In some embodiments, the presently disclosed subject matter is directed to a method of inserting a needle into the vessel of a patient. Specifically, the method comprises wrapping the cuff of a device at least partially around the limb of a patient. The device comprises a cuff comprising a plurality of side edges, a top face, and a bottom face. The device includes a first strap defined by a first end and a second end with a length therebetween, wherein the first end of the first strap is attached to a first side edge of the cuff. The device includes a second strap defined by a first end and a second end with a length therebetween, wherein the first end of the second strap is attached to a second side edge of the cuff, wherein the first cuff side edge is directly opposed to the second side edge of the cuff. The method comprises wrapping the second ends of the first and second straps at least one time about an outer surface of the cuff. The method comprises securing the second ends of the first and second straps together to create a pressure about the circumference of the cuff, wherein the pressure exposes the vessel in the limb of the patient, and inserting a needle into the vessel.

In some embodiments, the needle is inserted to draw blood from the vessel, inject a substance into the vessel, or insert an IV line into the vessel.

In some embodiments, the second ends of the first and second straps are tied together.

In some embodiments, the first end of the first strap and the first end of the second strap are separated by about 180 degrees when attached to a cuff.

BRIEF DESCRIPTION OF THE DRAWINGS

The previous summary and the following detailed descriptions are to be read in view of the drawings, which illustrate some (but not all) embodiments of the presently disclosed subject matter.

DETAILED DESCRIPTION

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

Figure 1:
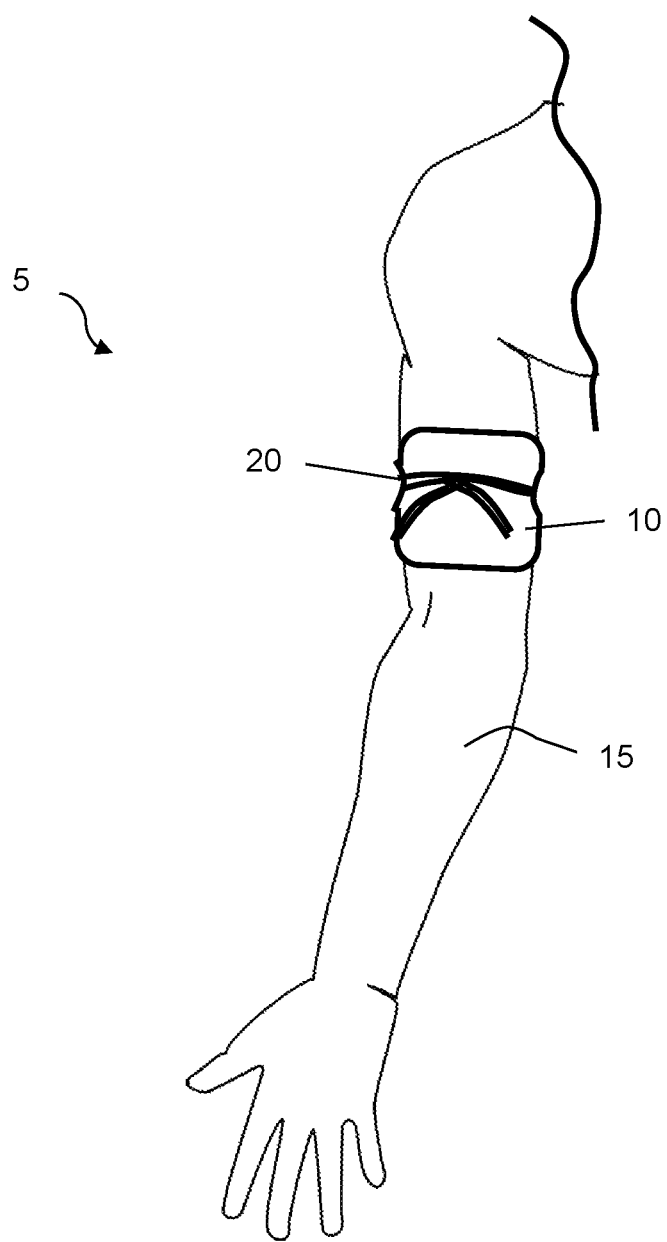
FIG. 1 is a perspective view of a device in use in accordance with some embodiments of the presently disclosed subject matter.

The presently disclosed subject matter is generally directed to a device that can be used as a tourniquet cuff for effective blood draws and intravenous (IV) line insertion. The disclosed device assists skilled medical professionals in locating a vessel (such as a vein or artery) and inserting an IV line, catheter, and/or blood drawing needle therein. As shown in FIG. 1, device 5 includes cuff 10 that wraps around at least a portion of patient limb 15 (e.g., an arm or leg). The cuff is secured on the patient's limb with straps 20 that are tightened and maintained about the circumference of the cuff. When the device is configured on the limb of a patient, the patient's blood vessels (e.g., veins) immediately engorge with blood. In this way, the vessels can be clearly visualized and/or accessed by a medical professional. As a result, blood can easily and efficiently be drawn and/or an IV line successfully inserted without multiple attempts at finding the vessel.

Figure 2:
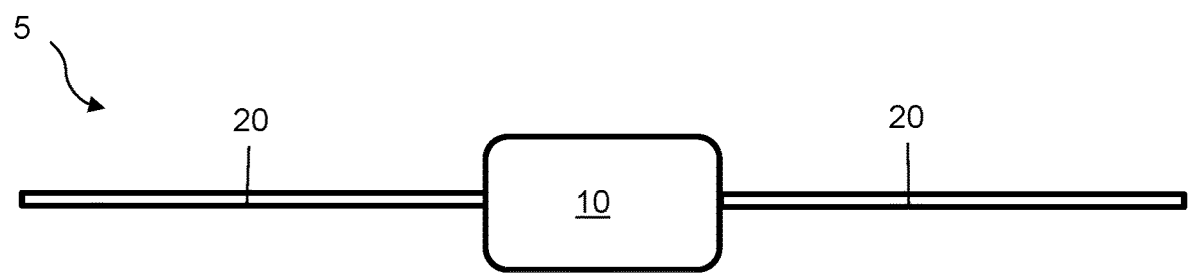
FIG. 2 is a top plan view of a device in accordance with some embodiments of the presently disclosed subject matter.

FIG. 2 illustrates one embodiment of device 5. Particularly, the device includes cuff 10 and straps 20. The cuff can be constructed as a band positioned in the approximate center portion of the device, with a pair of straps attached at each end. Cuff 10 can be constructed in any desired shape, such as (but not limited to) rectangular, square, oval, circular, hexagonal, pentagonal, octagonal, abstract, and the like. The cuff can also be configured to have a variety of known shapes, such as flowers, animals, cartoon characters, and the like, which can be useful when using the device with children.

Figure 3A:
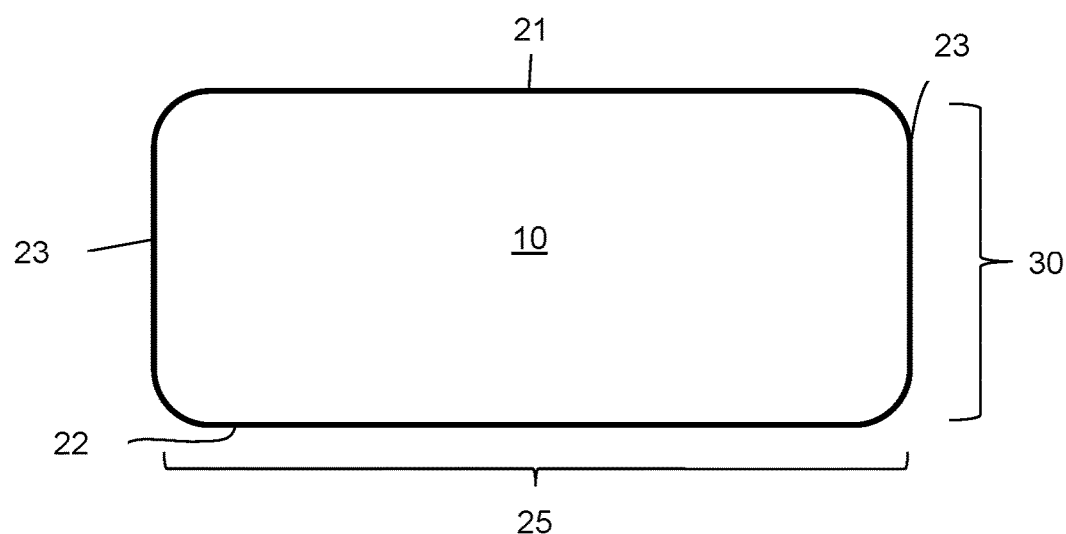
FIG. 3a is a top plan view of a device cuff in accordance with some embodiments of the presently disclosed subject matter.

Cuff 10 includes length 25 and width 30, as illustrated in FIG. 3a. The term "length" refers to the maximum dimension of the cuff in the longitudinal direction. The term "width" refers to the maximum dimension of the cuff perpendicular to the length. In some embodiments, the cuff can have a length of about 5-10 inches, such as at least about (or no more than about) 5, 5.5, 6, 6.5, 7, 7.5, 8, 8.5, 9, 9.5, or 10 inches. Similarly, the cuff can have a width of about 2-6 inches (e.g., at least/no more than about 2, 2.5, 3, 3.5, 4, 4.5, 5, 5.5, or 6 inches). However, it should be appreciated that the presently disclosed subject matter is not limited and the cuff length and width can be configured outside the ranges given above.

Figure 3B:
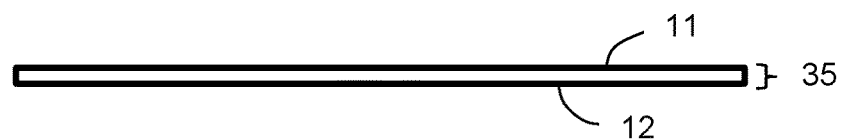
FIG. 3b is a side plan view of the device cuff of FIG. 3a in accordance with some embodiments of the presently disclosed subject matter.

The cuff further includes top face 11, bottom face 12, and thickness 35, as shown in FIG. 3b. The "top face" refers to the face that is positioned away from the patient, opposing the bottom face. The "bottom face" refers to the face that is adjacent to the patient. The term "thickness" refers to the longest dimension of the cuff perpendicular to both the length and width. The cuff can be configured with any desired thickness, such about 0.03-1 inch. Thus, the cuff can have a thickness of at least about (or no more than about) 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 inch. However, the thickness of the cuff is not limited and can be constructed with any desired thickness.

The length, width, and/or thickness of the cuff can be available in a variety of standard sizes depending on a particular patient. For example, cuff 10 can be constructed in multiple sizes to accommodate babies, children, and adults. In addition, obese and muscular patients typically have arms with circumferences that are larger than an average patient, requiring a larger sized cuff.

Cuff 10 includes at least one edge. For example, the cuff can include top edge 21, opposed bottom edge 22, and first and second side edges 23, as shown in FIG. 3a. As described in detail below, one end of each strap is attached to an edge of the cuff using any of a wide variety of techniques. For instance, one end of each strap can be attached to a cuff side edge.

Cuff 10 can be constructed from any desired material, such as (but not limited to) an elastic material. The term "elastic" refers to a material that can be stretched or deformed and still return to its original shape without significant deformation. In some embodiments, the elastic material can be expanded without breaking when stretched to at least 50% of its original unstretched length in at least one direction. Suitable elastic materials can include rubber, stretchable fabric, ethylene vinyl acetate, EPM (ethylene propylene rubber), polybutadiene, thermoplastic elastomers, perfluoroelastomers, polyether block amides, fluorosilicone rubber, polyacrylic rubber, or combinations thereof. However, the cuff can be constructed from any suitable elastic or non-elastic material, such as (but not limited to) plastic, fabric, or combinations thereof.

In some embodiments, the material used to construct the cuff (and/or strap) can be a medically approved material. Specifically, the material can be highly flexible, durable, and suitable for contact with the skin of a patient. In some embodiments, the materials can be tear-resistant to allow for conventional use.

In some embodiments, the cuff is latex-free. The term "latex" refers to a stable dispersion (emulsion) of polymer microparticles in water. Some patients are allergic to latex, such that it would be beneficial for device 5 to be configured as a latex-free device.

Figure 3C:
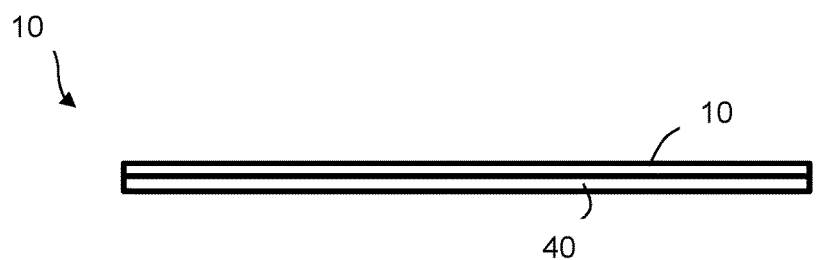
FIGS. 3c and 3d are side plan views of a device cuff comprising padding in accordance with some embodiments of the presently disclosed subject matter.
Figure 3D:
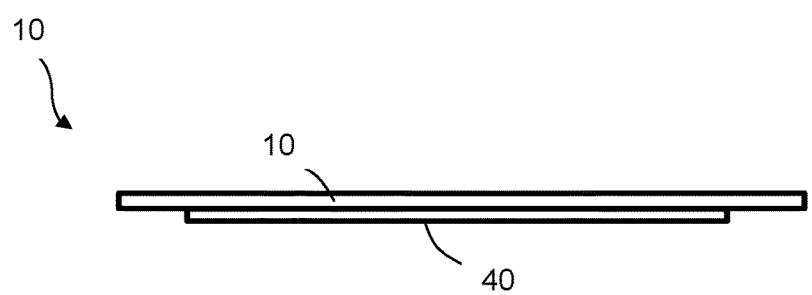

In some embodiments, top face 11 and/or bottom face 12 of the cuff can include padding 40 to provide an additional cushioning element for patient comfort. Padding 40 can include (but is not limited to) any rubber, fabric, mesh, foam, silicone, and/or similar material. The padding can fully or partially extend along the length of the cuff, as shown in FIGS. 3c and 3d. For example, the padding can extend about 25-100% of the length of the cuff (e.g., at least/no more than about 25, 30, 35, 40, 45, 55, 60, 65, 70, 75, 80, 85, 90, 95, or 100 percent of the length of the cuff).

Alternatively or in addition, at least one face 11 or 12 of the cuff can be coated to prevent or reduce irritation when coming into contact with the patient's skin. Suitable coatings can include (but are not limited to) polymeric material, wax, fabric, mesh, and the like. It should be appreciated that the coating is optional, and the cuff can be configured without a coating.

Figure 4A:
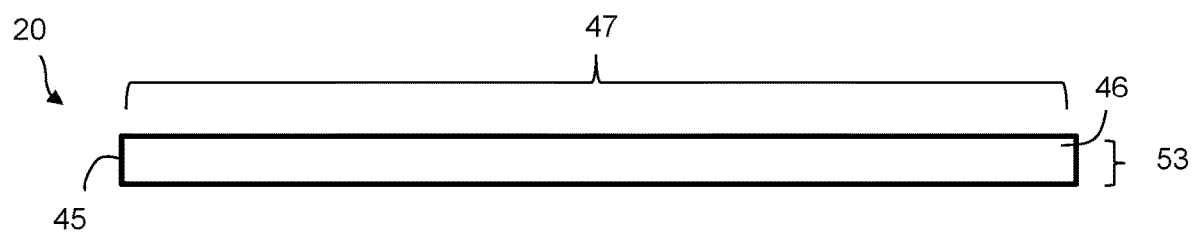
FIG. 4a is a top plan view of a device strap in accordance with some embodiments of the presently disclosed subject matter.
Figure 4B:
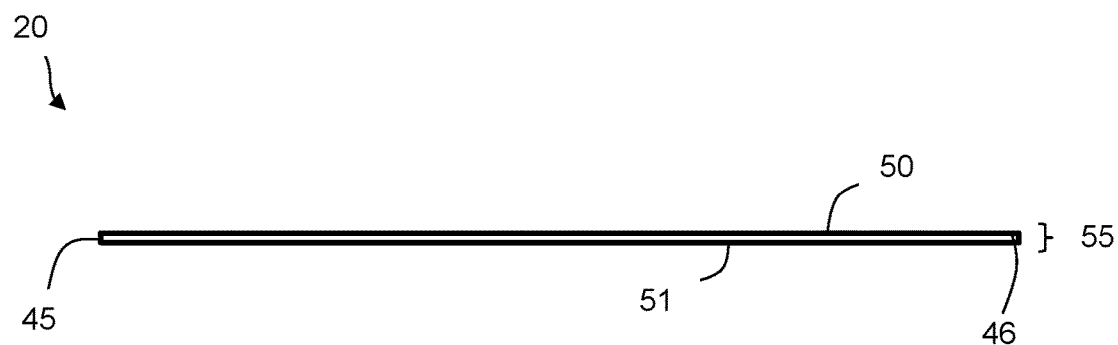
FIG. 4b is a side plan view of a device strap in accordance with some embodiments of the presently disclosed subject matter.

As set forth above, device 5 includes a plurality of straps 20 that are attached to each end of cuff 10. The straps are configured to wrap around the cuff at least one time and be secured together. FIGS. 4a and 4b illustrate one embodiment of strap 20. As illustrated, the strap includes first and second ends 45, 46 with length 47 therebetween. Each strap also includes top face 50 and opposing bottom face 51.

Each strap can have a length 47 of about 20-60 inches. Thus, the strap can have a length of at least about (or no more than about) 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 inches. However, the strap length can be longer or shorter than the range given above. In some embodiments, the length of a particular strap can be adjusted. In this way, a strap can be customized for a particular patient. Any known mechanism can be used to adjust the length of a strap, such as buckles, clips, and the like.

Each strap can further include width 53 of about 0.5-2 inches. Thus, the strap width can be at least about (or no more than about) 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 inches. However, the presently disclosed subject matter is not limited and the strap can have a width greater or less than the given range.

Figure 4C:
FIG. 4c is a side plan view of a tapered device strap in accordance with some embodiments of the presently disclosed subject matter.

In some embodiments, each strap includes a uniform width about the length of the strap. In other embodiments, strap 20 can taper, as shown in FIG. 4c.

Strap 20 includes thickness 55, as illustrated in FIG. 4b. Thickness 55 can be at least about (or no more than about) 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 inch. However, it should be appreciated that the thickness of straps 20 are not limited and can be configured with any dimensions.

Figure 5:
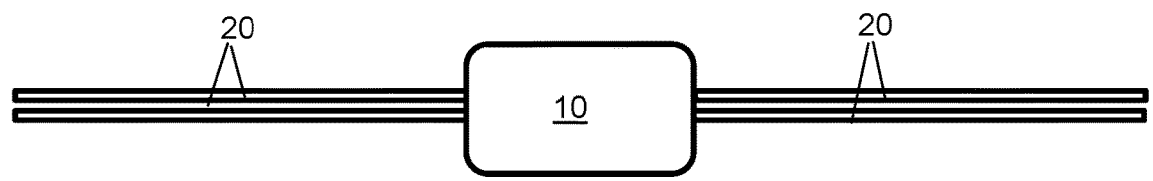
FIG. 5 is a top plan view of a device comprising a plurality of straps in accordance with some embodiments of the presently disclosed subject matter.

Device 5 can include any number of straps 20. For example, in some embodiments, the device includes two straps attached to two opposing side edges of the cuff, as shown in FIG. 2. However, the device can include more than two straps such that their properties combine to provide a desired property, as shown in the embodiment of FIG. 5. Device 5 can therefore include any number of straps (e.g., 1-4 or more).

In some embodiments, each strap is constructed with about the same length, width, and/or thickness relative to at least one other strap. However, the presently disclosed subject matter is not limited and can include embodiments wherein each strap has a unique length, width, and/or thickness compared to another strap.

Any of a wide variety of materials can be used to construct straps 20. For example, one or more elastic materials can be used, such as rubber, stretchable fabric, ethylene vinyl acetate, EPM (ethylene propylene rubber), polybutadiene, thermoplastic elastomers, perfluoroelastomers, polyether block amides, fluorosilicone rubber, polyacrylic rubber, or combinations thereof. However, the straps can be constructed from any suitable material, such as (but not limited to) plastic, fabric, or combinations thereof. The material used to construct the strap can comprise non-elastic materials or combinations of elastic and non-elastic materials (e.g., cloths, fabrics, threads, or struts combined with an elastic material through sewing, adhesives, and the like).

In some embodiments, the materials used to construct straps 20 are free from latex.

Figure 6A:
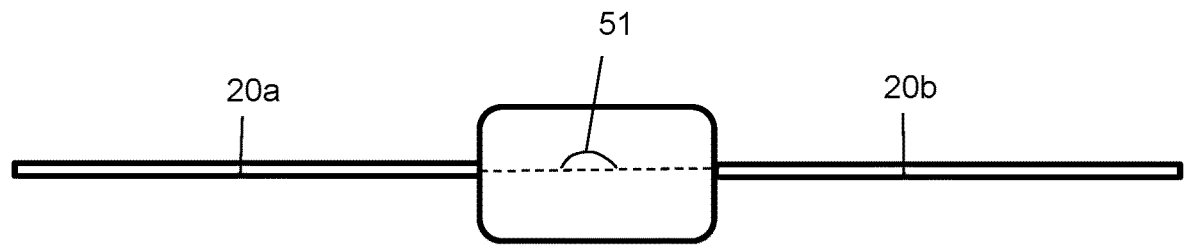
FIG. 6a is a top plan view of a device with opposed straps in accordance with some embodiments of the presently disclosed subject matter.
Figure 6B:
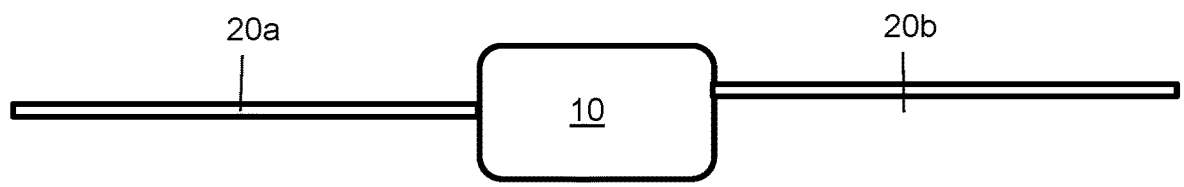
FIG. 6b is a top plan view of a device with offset straps in accordance with some embodiments of the presently disclosed subject matter.

The first end of each strap is permanently or releasably attached to one edge of cuff 10. For example, the straps can be attached to opposing side edges or faces of the cuff, as shown in the embodiment of FIG. 6a. Thus, first strap 20a can be separated from second strap 20b by angle 51 of about 180 degrees (e.g., at least/no more than about 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, or 255 degrees). The straps can be positioned in the approximate center of a corresponding cuff edge. Alternatively, first strap 20*a* can be offset from second strap 20*b* as shown in FIG. 6*b*.

The straps can be permanently or releasably attached to the cuff using any known mechanism, such as the use of heat sealing, sewing, adhesives, ultrasonic welding, RF welding, VELCRO®, magnets, mechanical elements (e.g., buttons, hooks, snaps, buckles). Alternatively, device 5 can be formed as a single unit with the straps pre-formed with the cuff using known techniques, such as thermoforming and the like.

In some embodiments, device 5 is disposable. The term "disposable" refers to the characteristic of being used a single time with a single patient and then discarded or recycled. However, the presently disclosed subject matter also includes embodiments wherein device 5 is sterilized and/or cleaned for reuse with another patient(s).

The device can be configured in any desired color (black, blue, grey, white, yellow, pink, red, orange, green, purple, etc.) and/or any desired pattern (stripes, polka dots, chevon, etc.). The device can further include graphics or writing, such as instructions for use, trade names, and the like.

Figure 7:
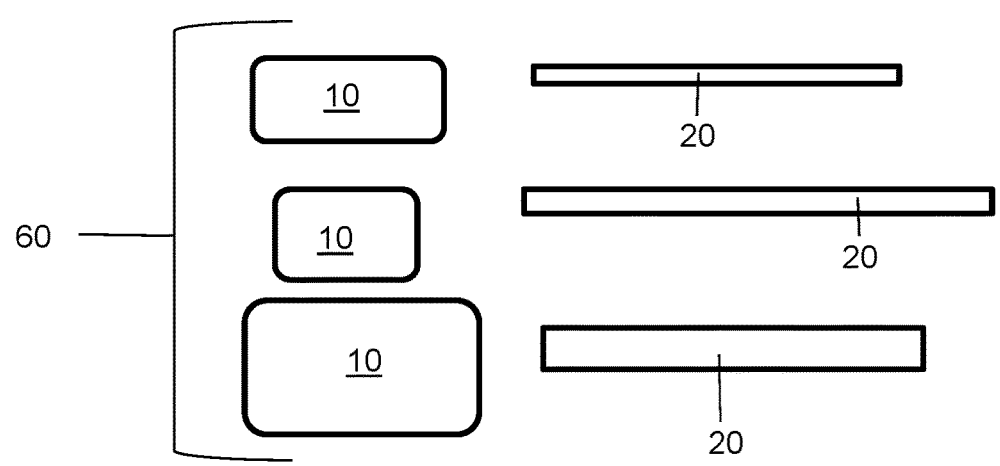
FIG. 7 is a schematic of a kit in accordance with some embodiments of the presently disclosed subject matter.

In some embodiments, device 5 can be configured in a kit. Specifically, kit 60 can include a variety of cuffs and straps of varying shapes, materials, elasticity, and/or sizes. A particular device can then be customized based on a patient. For example, an overweight patient will require a larger sized cuff and longer straps compared to a child. FIG. 7 illustrates one embodiment of kit 60. Any number of cuffs 10 and straps 20 can be included. Thus, the kit can include a variety of cuffs and straps that are mixed and matched depending on a particular patient's need. The kit can further include one or more pre-assembled devices suitable for a particular patient population (children, adults, etc.).

In practice, device 5 can be used to assist medical professionals in visualizing and accessing vessels in a patient. As described above, the visualization and accessing of vessels in some patients has proven challenging. For example, the vessels of obese patients are often difficult to access due to excess amounts of fatty tissue and skin. In addition, burn victims have a surplus of scar tissue, which can make locating vessels challenging. The vessels of children are relatively small and therefore can be difficult to locate. Further, elderly or ailing patients with low blood pressure have vessels that are difficult to locate.

Figure 8A:
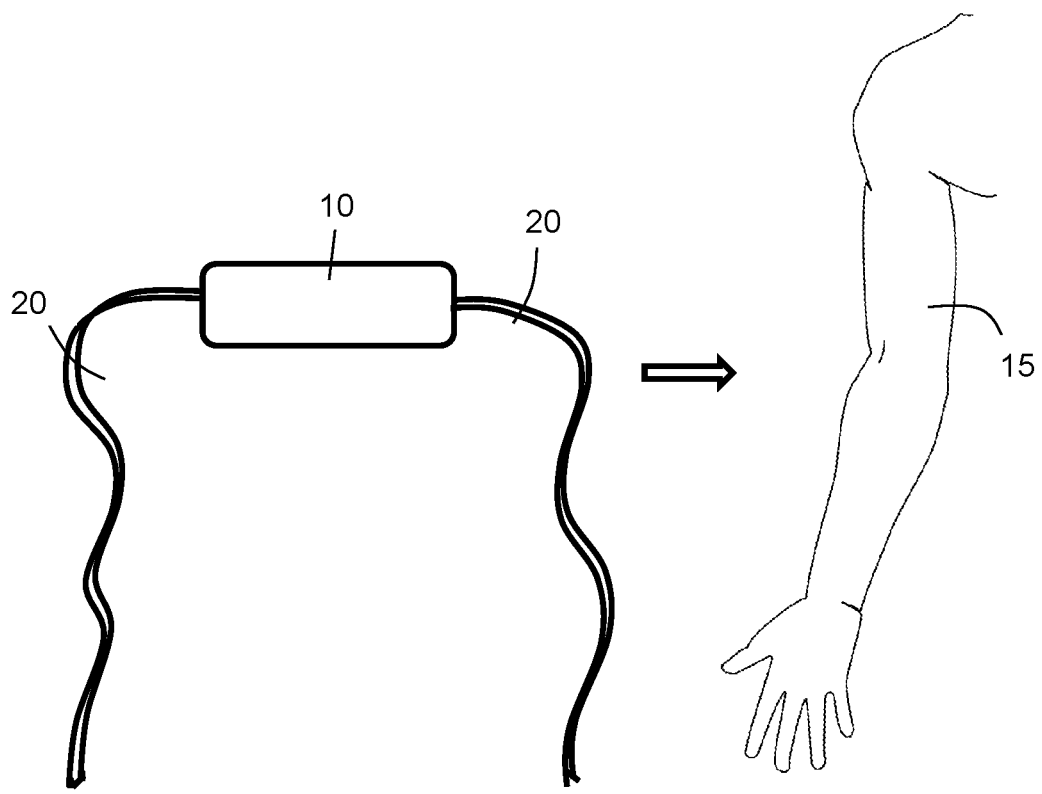
FIGS. 8a-8d are front plan views illustrating one method of using the device in accordance with some embodiments of the presently disclosed subject matter.
Figure 8B:
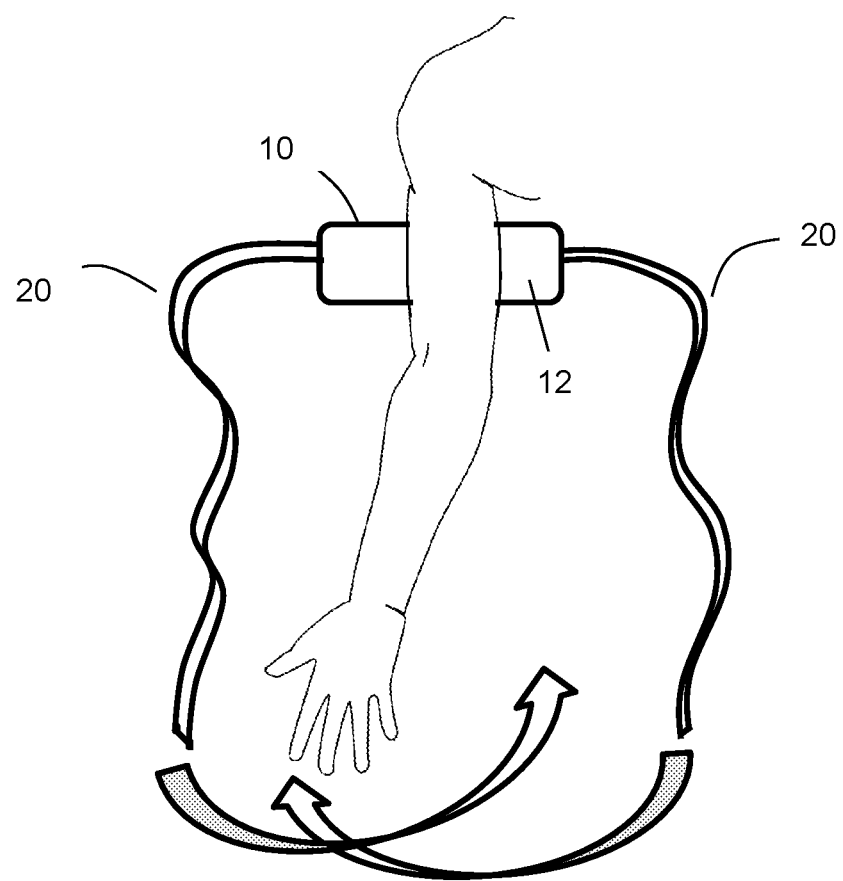
Figure 8C:
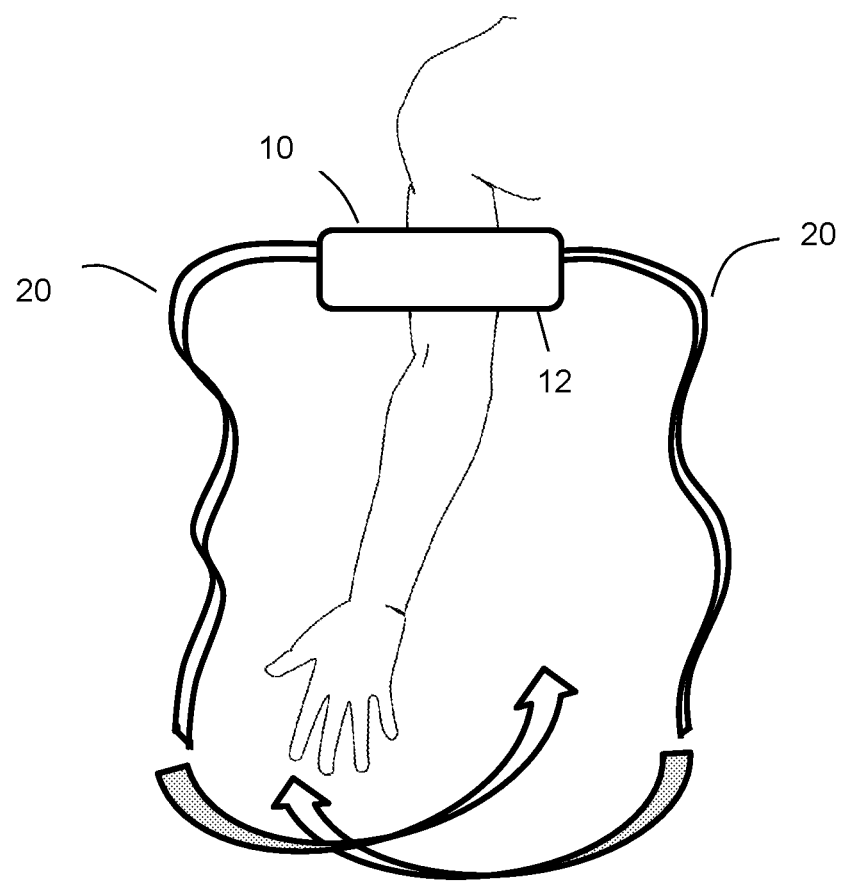
Figure 8D:
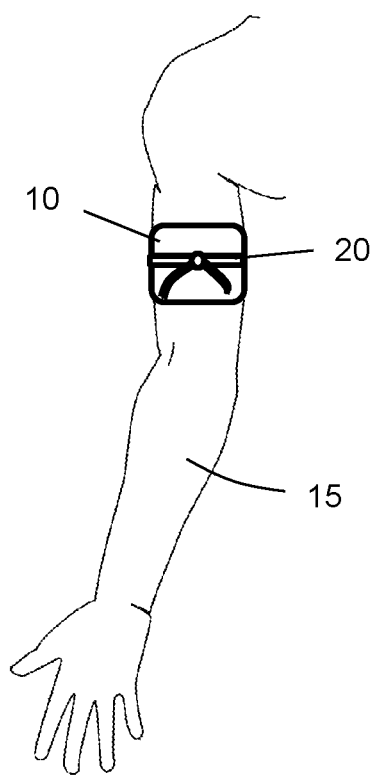

In use, the device is positioned such that cuff 10 is wrapped at least partially around the limb of a patient (e.g., arm), as shown in FIGS. 8*a* and 8*b*. The cuff can be positioned on the top or bottom of the arm, as shown in FIGS. 8*b* and 8*c*. Bottom face 12 of the cuff is positioned adjacent to the patient's skin or clothing. The cuff is then configured to wrap around the patient's limb and is held in position as straps 20 are wrapped around the outer surface of the cuff, as shown in FIG. 8*c*. The straps therefore encircle the patient's limb about the cuff. For example, in some embodiments, the free strap ends can be tied together along the length of the straps to create a tight grip on the patient's arm, as shown in FIG. 8*d*.

The straps therefore create a squeezing pressure on the patient's arm. Instead of being directly concentrated on the patient's arm (and therefore painfully digging into and pinching the patient's arm), cuff 10 acts as a buffer, preventing injury and/or discomfort while also allowing the pressure to be maintained on the limb. Thus, the straps create an even pressure around the arm, but are prevented from digging into the patient's skin. The straps further tightly position the device on the limb of a patient, such that the cuff does not move around or slip.

The squeezing effect of the device on the limb of the patient creates an even pressure, which allows vessels in the patient's limb to become visible (e.g., the vessels are distended). In addition, because the cuff is wide and wraps at least partially around the patient's arm, the cuff is not uncomfortable to the patient, and does not push into the patient's skin. Thus, the proper amount of pressure is applied to the patient's arm without cutting off the blood flow (e.g., arterial flow) of the patient. The vessels are then visible and accessible. The skilled practitioner (e.g., nurse or phlebotomist) can then insert a needle into the vessel for drawing blood, insertion of medication, and/or an IV line can be easily attached. In this way, the vessel can be accessed, and the location of the vessel determined.

Figure 9:
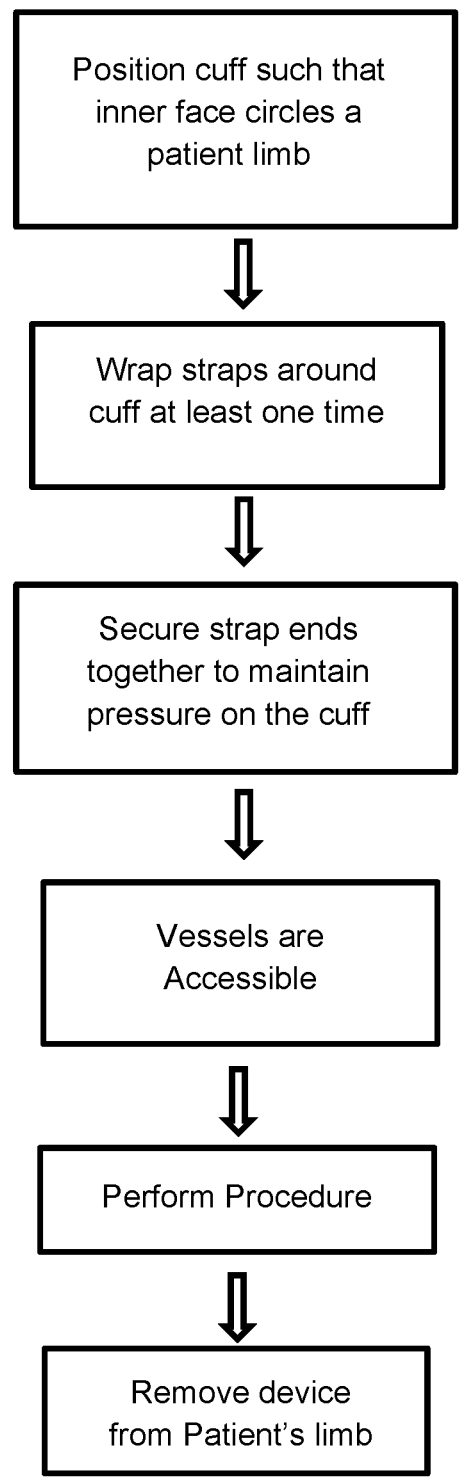
FIG. 9 is a diagram illustrating one method of using the device in accordance with some embodiments of the presently disclosed subject matter.

After the procedure is performed, the device can be removed from the patient's limb by freeing straps 20 and decoupling the cuff from the patient, as set forth in the schematic of FIG. 9.

Figure 10:
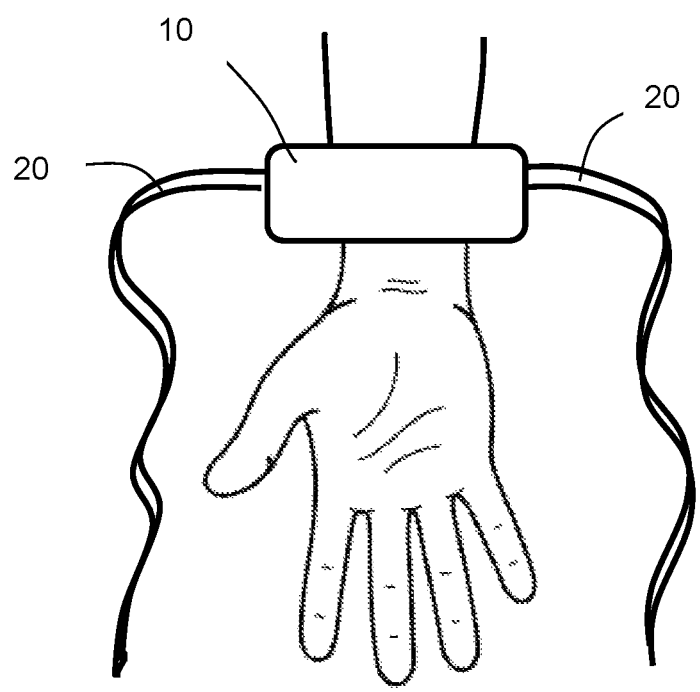
FIG. 10 is a top plan view of a device positioned on a patient's wrist in accordance with some embodiments of the presently disclosed subject matter.

Although primarily shown and described in use with a patient's arm, device 5 can be used with any limb. FIG. 10 illustrates one embodiment of device 5 configured about a patient's wrist for hand blood draws.

It should further be appreciated that the device can be used on humans as well as for veterinary use. Thus, the device can be used on dogs, cats, rabbits, and the like to visualize vessels as needed.

Although the presently disclosed subject matter has been primarily described for use with a needle, similar principles apply to the insertion of other objects into a vessel, such as catheters, tubes, shunts, and the like.

The disclosed device offers many improvements over prior art devices. Particularly, as described above, the device allows a skilled practitioner to determine the location of a blood vessel in a patient easily and effectively. As a result, the blood draw is less painful and more efficient, requiring fewer needle sticks to locate the vein.

The wide cuff prevents pinching of the patient's skin, which can be uncomfortable.

In addition, the disclosed device prevents or reduces the occurrence of arm hair being pulled or caught in the device.

Further, the device does not require an inflatable bladder. Rather, the tying of the straps provides adequate and even pressure to the patient's limb.

Device 5 is suitable with a wide range of patients. For example, the disclosed device can be effectively used healthy patients, as well as burn victims with veins that are difficult to access, patients with sensitive skin that easily bruises and tears, children, the elderly, and overweight/obese patients.

The disclosed device is also simple to use and does not require extensive training or expertise to use correctly.

While this invention has been particularly shown and described with references to preferred embodiments thereof, it will be understood by those skilled in the art that various changes in form and details may be made herein without departing from the spirit and scope of the invention as defined by the appended claims.

What is claimed is:

1. A device for use in visualizing blood vessels in a patient, the device comprising:
   a cuff comprising a top face, a bottom face, a top edge, and an opposed bottom edge, a first side edge and a second side edge, wherein the top and bottom edges have a length that is greater than the length of the first and second side edges;

a first strap defined by a first end and a second end with a length therebetween, wherein the first end of the first strap is directly attached to the first side edge of the cuff; and a second strap defined by a first end and a second end with a length therebetween, wherein the first end of the second strap is directly attached to the second side edge of the cuff;

wherein the cuff and first and second straps are configured to fully wrap around a limb of the patient.

2. The device of claim 1, wherein the first end of the first strap and the first end of the second strap are separated by about 180 degrees.

3. The device of claim 1, wherein the cuff has a length of about 5-10 inches, a width of about 2-6 inches, and a thickness of about 0.03-1 inch.

4. The device of claim 1, wherein the first and second straps each have a length of about 20-60 inches, a width of about 0.5-2 inches, and a thickness of about 0.03-1 inch.

5. The device of claim 1, wherein at least one of the first strap, second strap, and cuff are constructed from an elastic material.

6. The device of claim 1, wherein the bottom face of the cuff comprises a padding material selected from foam, polymeric material, mesh, rubber, silicone, or combinations thereof.

7. The device of claim 1, wherein the first end of the first strap and the first end of the second strap are offset.

8. The device of claim 1, wherein the first end of the first strap and the second end of the second strap are separated by greater than 180 degrees.

9. The device of claim 1, wherein each strap includes a width that tapers from the first end to the second end.

10. A kit comprising:
a plurality of cuffs, each cuff defined by a top face, a bottom face, a top edge, and an opposed bottom edge, a first side edge and a second side edge, wherein the top and bottom edges have a length that is greater than the length of the first and second side edges;

a plurality of straps, each strap comprising a first end and a second end with a length therebetween;

wherein the first end of each strap is releasably attachable to a side edge of a corresponding cuff; and wherein the plurality of cuffs and straps are configured in a variety of shapes, sizes, materials, or combinations thereof, and wherein the first strap end is configured to directly attach to a first cuff side edge, and the second strap end is configured to directly attach to a second cuff side edge, and wherein the cuff and first and second straps are configured to fully wrap around a limb of the patient.

11. The kit of claim 10, wherein each cuff has a length of about 5-10 inches, a width of about 2-6 inches, and a thickness of about 0.03-1 inch.

12. The kit of claim 10, wherein each strap has a length of about 20-60 inches, a width of about 0.5-2 inches, and a thickness of about 0.03-1 inch.

13. The kit of claim 10, wherein at least one strap and cuff are constructed from an elastic material.

14. A method of inserting a needle into the vessel of a patient, the method comprising:
wrapping the cuff of a device fully around the limb of a patient, wherein the device comprises:
a cuff comprising a top face, a bottom face, a top edge, and an opposed bottom edge, a first side edge and a second side edge, wherein the top and bottom edges have a length that is greater than the length of the first and second side edges;

a first strap defined by a first end and a second end with a length therebetween, wherein the first end of the first strap is directly attached to the first side edge of the cuff; and a second strap defined by a first end and a second end with a length therebetween, wherein the first end of the second strap is directly attached to the second side edge of the cuff;

wherein the cuff and first and second straps are configured to fully wrap around a limb of the patient;

wrapping the second ends of the first and second straps at least one time about an outer surface of the cuff;

securing the second ends of the first and second straps together to create a pressure about the circumference of the cuff, wherein the pressure exposes the vessel in the limb of the patient; and inserting a needle into the vessel.

15. The method of claim 14, wherein the needle is inserted to draw blood from the vessel, inject a substance into the vessel, or insert an IV line into the vessel.

16. The method of claim 14, wherein the second ends of the first and second straps are tied together.

17. The method of claim 14, wherein the first end of the first strap and the first end of the second strap are separated by about 180 degrees.

18. The method of claim 14, wherein the cuff has a length of about 5-10 inches, a width of about 2-6 inches, and a thickness of about 0.03-1 inch.

19. The method of claim 14, wherein the first and second straps each have a length of about 20-60 inches, a width of about 0.5-2 inches, and a thickness of about 0.03-1 inch.

20. The method of claim 14, wherein at least one of the first strap, second strap, and cuff are constructed from an elastic material.

* * * * *